(12) United States Patent
Veronese et al.

(10) Patent No.: US 10,626,102 B2
(45) Date of Patent: Apr. 21, 2020

(54) PROCESS FOR THE SYNTHESIS OF EFINACONAZOL

(71) Applicant: Procos S.P.A.

(72) Inventors: Martino Veronese, Castano Primo (IT); Piergiorgio Bettoni, Casale Monferrato (IT); Jacopo Roletto, Turin (IT); Paolo Paissoni, Druento (IT)

(73) Assignee: Procos S.P.A., Cameri (IT)

( * ) Notice: Subject to any disclaimer, the term of this patent is extended or adjusted under 35 U.S.C. 154(b) by 0 days.

(21) Appl. No.: 16/066,328

(22) PCT Filed: Dec. 22, 2016

(86) PCT No.: PCT/EP2016/082345
§ 371 (c)(1),
(2) Date: Jun. 27, 2018

(87) PCT Pub. No.: WO2017/114743
PCT Pub. Date: Jul. 6, 2017

(65) Prior Publication Data
US 2019/0010141 A1 Jan. 10, 2019

(30) Foreign Application Priority Data
Dec. 30, 2015 (IT) .................. 102015000089243

(51) Int. Cl.
C07D 401/06 (2006.01)
(52) U.S. Cl.
CPC .................. C07D 401/06 (2013.01)
(58) Field of Classification Search
CPC .................................. C07D 401/06
USPC ....................................... 546/210
See application file for complete search history.

(56) References Cited

U.S. PATENT DOCUMENTS 8,871,942 B2 * 10/2014 Mimura ............. C07D 401/06
546/210
2018/0118714 A1 * 5/2018 Sasane ................ C07D 401/06

FOREIGN PATENT DOCUMENTS

| EP | 0698606 A1 | 2/1996 | | |
|---|---|---|---|---|
| EP | 2612859 A1 * | 7/2013 | .......... | C07D 401/06 |
| EP | 2612859 A1 | 7/2013 | | |
| WO | WO-2016079728 A1 * | 5/2016 | ............. | C07C 17/35 |

OTHER PUBLICATIONS

Metal Salts as new catalyst for mild and efficient aminolysis of oxiranes, Maroo Chini et al. Tetrahedron letters, vol. 31, No. 32, pp. 4661-4664 (Year: 1990).*
J. Org. Chem., vol. 56, No. 20, Marco Chini et al, Regioalternating Selectivity in the metal Salt Catalysed Aminilysis of Styrene oxide (Year: 1991).*
James Ashenhurst, Grignard reagents in Organic agents (Year: 2011).*
Ogura H. et al., "Synthesis and antifungal activites of (2R,3R)-2-aryl-1-azolyl-3-(substitut ed amino)-2-butanol derivatives as topical antifungal agents", Chemical and Pharmaceutical Bulletin, vol. 47, No. 10, Oct. 1, 1999, pp. 1417-1425.
Search Report and Written Opinion of PCT/EP2016/082345 dated Feb. 28, 2017.

* cited by examiner

Primary Examiner — Rita J Desai
(74) Attorney, Agent, or Firm — Silvia Salvadori, P.C.; Silvia Salvadori

(57) ABSTRACT

Disclosed is a process for the synthesis of efinaconazole (I), starting from 1-[[(2R,3S)-2-(2,4-difluorophenyl)-3-methyloxiranyl]methyl]-1H-1,2,4-triazole and 4-methylenepiperidine, as free base or hydrochloride, in an organic solvent, under anhydrous conditions and in the presence of neutralising agents and reaction-promoting metal species. (1) The process is particularly advantageous because it gives rise to efinaconazole in high yields and purity, and uses little more than the stoichiometric amount of 4-methylenepiperidine, a rather expensive commercially available reagent.

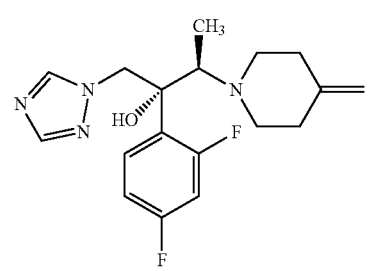

5 Claims, 3 Drawing Sheets

PROCESS FOR THE SYNTHESIS OF EFINACONAZOL

Figure 1:
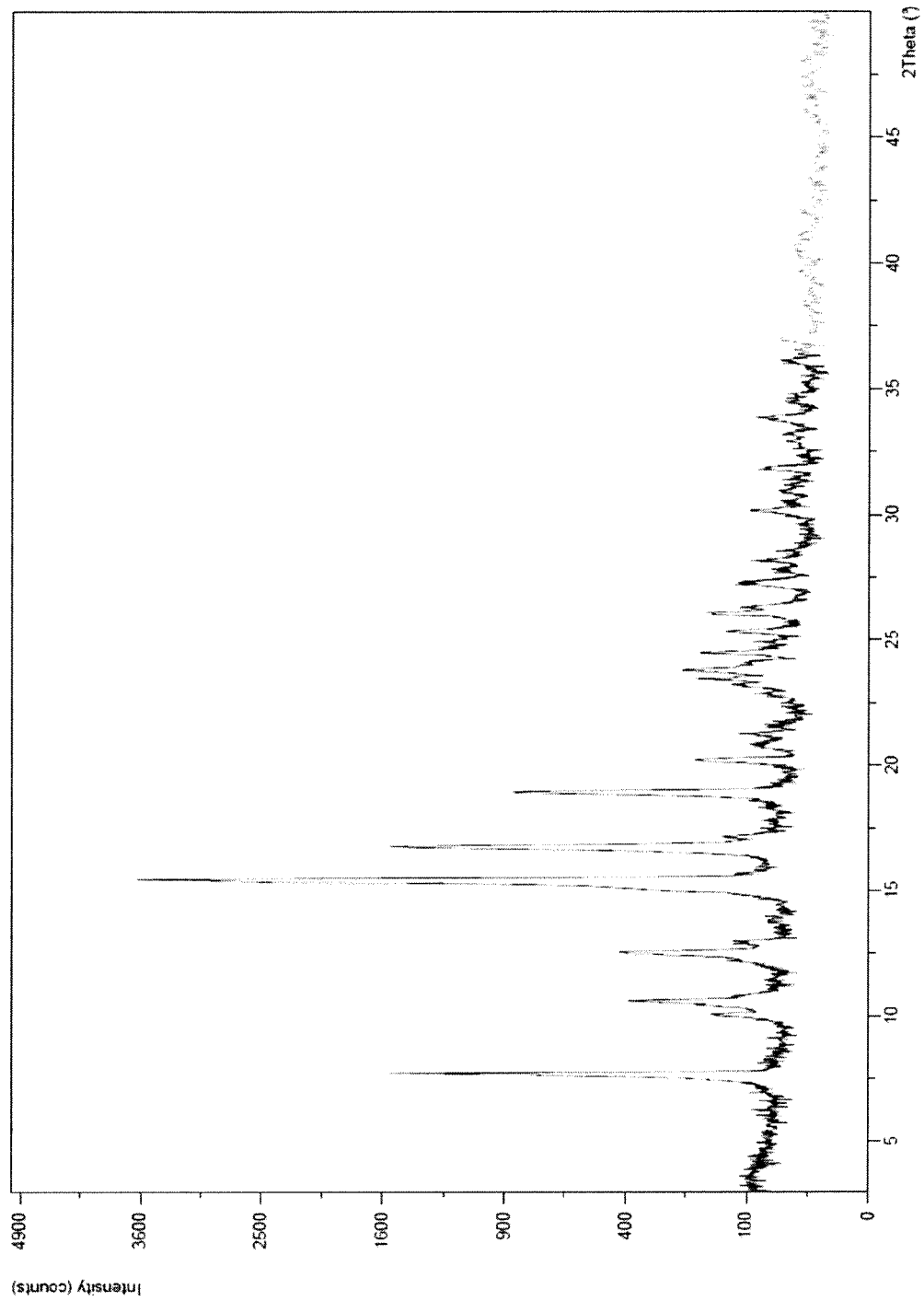

This application is a U.S. national stage of PCT/EP2016/082345 filed on 22 Dec. 2016, which claims priority to and the benefit of Italian Application No. 102015000089243 filed on 30 Dec. 2015, the contents of which are incorporated herein by reference in their entireties.

FIELD OF INVENTION

The object of the present invention is an advantageous process for the synthesis of efinaconazole.

BACKGROUND TO THE INVENTION

Many triazole derivatives are antimycotic agents which are widely used in the treatment of mycosis.

A number of patents report the synthesis of efinaconazole starting form 1-[[(2R,3S)-2-(2,4-difluorophenyl)-3-methyloxiranyl]methyl]-1H-1,2,4-triazole and 4-methylenepiperidine free base or hydrochloride.

WO9426734 reports the synthesis of efinaconazole starting from the intermediate 1-[[(2R,3S)-2-(2,4-difluorophenyl)-3-methyloxiranyl]methyl]-1H-1,2,4-triazole, whose epoxytriazole ring is opened by the use of a large excess (10 equivalents) of methylenepiperidine in the form of a hydrochloride suitably neutralised. Said opening reaction takes place in the absence of reaction-promoting metal species; the product is obtained in a yield of 54%.

The disadvantages of said process are the use of a large excess of methylenepiperidine (which is relatively expensive), and low yields. A further drawback is that methylenepiperidine free base is not commercially available, whereas the hydrochloride is available.

WO2012029836 discloses a process for obtaining efinaconazole starting from 1-[[(2R,3S)-2-(2,4-difluorophenyl)-3-methyloxiranyl]methyl]-1H-1,2,4-triazole and methylenepiperidine hydrobromide salt in the presence of metal hydroxides such as lithium, sodium, calcium or strontium hydroxide; methylenepiperidine is used in much smaller amounts (1.5 equivalents) than the large excess used in WO9426734. The end product is obtained in a yield of 87%. Although efinaconazole is obtained in higher yields, the use of metal hydroxides (lithium, sodium, calcium and strontium) generates, in the release of methylenepiperidine base, the formation of water which reduces the quality (the purity of the isolated product is about 95%) and the yield when the end product is isolated. The reason is that the water present in the reaction competes with methylenepiperidine in the epoxide ring opening, causing hydrolysis of the latter with a consequent loss of yield and quality of the finished product.

On the basis of the available information there is an evident need for a more efficient process for the industrial production of efinaconazole.

DESCRIPTION OF THE INVENTION

The present invention relates to a process for the synthesis of efinaconazole (I) starting from intermediate 1-[[(2R,3S)-2-(2,4-difluorophenyl)-3-methyloxiranyl]methyl]-1H-1,2,4-triazole (II) and 4-methylenepiperidine, as free base (III) or hydrochloride (IV), in organic solvent in the presence of neutralising agents and reaction-promoting metal species under anhydrous conditions.

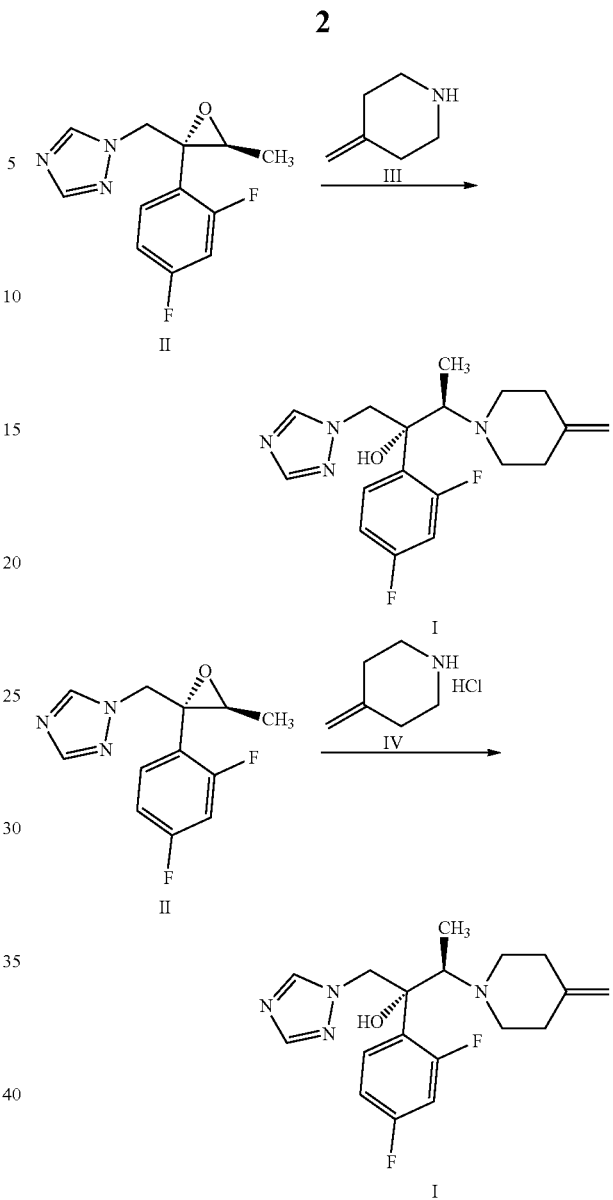

The process can be effected with the intermediate epoxytriazole (II) and methylenepiperidine hydrochloride salt (IV), directly generating the corresponding free base (III) in situ. Methylenepiperidine free base (III) can be generated in situ from the corresponding hydrochloride (IV) with the use of alkyl magnesium halides, preferably isopropylmagnesium bromide and chloride; optionally, said reaction can be effected with organic amines, preferably such as N,N-diisopropylethylamine (DIPEA) and anhydrous magnesium chloride ($MgCl_2$).

Optionally, efinaconazole is obtained by reacting intermediate (II) with methylenepiperidine in the form of free base (III), previously obtained by neutralising the corresponding hydrochloride (IV) with alkyl magnesium halides, preferably isopropylmagnesium bromide and chloride, or organic amines, preferably N,N-diisopropylethylamine (DIPEA).

The reaction is effected in an anhydrous aprotic organic solvent, preferably acetonitrile or tetrahydrofuran or 2-methyltetrahydrofuran.

It has now surprisingly been found that by carrying out the reaction as described in its embodiments under anhydrous conditions in the presence of suitable neutralising agents, efinaconazole is obtained in shorter times in high yields and quality (>99%).

Said neutralising agents can be selected from organic amines, preferably N,N-diisopropylethylamine (DIPEA) or alkyl magnesium halides such as isopropylmagnesium bromide or chloride.

According to a second aspect of the invention, efinaconazole can be obtained by reacting 1-[[(2R,3S)-2-(2,4-difluorophenyl)-3-methyloxiranyl]methyl]-1H-1,2,4-triazole (II) with methylenepiperidine hydrochloride (IV) in tetrahydrofuran in the presence of isopropylmagnesium bromide or chloride, neutralising agents responsible for releasing methylenepiperidine free base (III) in situ.

In one embodiment on the invention, efinaconazole can be obtained by performing the epoxide ring-opening reaction in acetonitrile, using methylenepiperidine hydrochloride which is neutralised in situ by the organic amine N,N-diisopropylethylamine (DIPEA) and anhydrous magnesium chloride ($MgCl_2$).

According to another embodiment on the process, efinaconazole is obtained by reacting intermediate 1-[[(2R,3S)-2-(2,4-difluorophenyl)-3-methyloxiranyl]methyl]-1H-1,2,4-triazole (II) in acetonitrile with a suspension of methylenepiperidine free base (III) previously obtained by neutralising the corresponding hydrochloride (IV) with suitable neutralising agents such as N,N-diisopropylethylamine (DIPEA) and anhydrous magnesium chloride ($MgCl_2$) as the source of metal species; said reaction can optionally be effected in tetrahydrofuran or 2-methyltetrahydrofuran and in the presence of isopropylmagnesium chloride.

The process is preferably carried out as follows.

The intermediate 1-[[(2R,3S)-2-(2,4-difluorophenyl)-3-methyloxiranyl]-methyl]-1H-1,2,4-triazole (II) is dissolved in 2-6 volumes of anhydrous acetonitrile, preferably 3-5 volumes relative to the amount of starting intermediate. 1.1-1.5 Moles of methylenepiperidine hydrochloride (IV), preferably 1.2-1.4 moles relative to the moles of the starting intermediate epoxytriazole, are added to the solution. 1.2-1.6 Moles of N,N-diisopropylethylamine (DIPEA), preferably 1.3-1.5 moles relative to the moles of the starting intermediate epoxytriazole, are added to the resulting suspension. The reaction is cooled to a temperature not exceeding 10° C., preferably to a temperature ranging from 2° C. to 6° C., and anhydrous magnesium chloride is then added gradually, in aliquots of 0.25-0.80 moles at a time, preferably 0.40-0.67 moles, for a total of 8-2.5 portions, preferably 5-3 portions (exothermic reaction).

The reaction mixture is heated to a temperature ranging from 60° C. to 85° C., preferably from 70° C. to 75° C., and said temperature is maintained until completion of the reaction, which is then monitored by UPLC analysis using an ACQUITY BEH C18 column with a water/acetonitrile/0.1% formic acid mixture as eluent phase.

After completion of the reaction, the reaction mixture containing efinaconazole (I) is concentrated; the resulting residue is dissolved in a mixture of water and organic solvent, preferably ethyl acetate (exothermic reaction); the organic phase is then filtered to remove the salts and insoluble particles and concentrated to obtain an oil. The resulting oily residue is dissolved in an alcohol solvent, preferably ethyl alcohol, to obtain a final concentration of 1.0-3.0 volumes of ethanol relative to the expected product, preferably 1.5-2.5 volumes. The solution is heated to a temperature ranging from 15 to 30° C., preferably from 20 to 25° C., and water is dropped therein in the ratio of 1.0-2.2 volumes relative to the expected product, preferably 1.4-1.8 volumes. The mixture is cooled again to a temperature below 10° C., preferably 0-5° C.; it is then filtered and washed with a water/ethanol mixture. The resulting solid is dried under vacuum at the temperature of 45° C.-55° C. to obtain crude efinaconazole which can be purified by salting with organic acids such as para-toluenesulphonic acid, followed by release and final isolation. The crude efinaconazole can optionally be purified with alkyl hydrocarbons such as heptane.

Typically, the crude efinaconazole is dissolved in 3.0-6.0 volumes of a polar aprotic solvent such as ethanol or isopropanol, preferably 4.0-5.0 volumes. The solution is heated to 40-60° C., preferably 45-55° C., and 0.9-1.1 moles of para-toluenesulphonic acid, preferably 0.95-1.05 moles, are dropped therein at said temperature. The reaction mixture is first refluxed then cooled to a temperature below 10° C., preferably 0-5° C.; the suspension is then filtered and washed. The resulting solid is dried under vacuum at the temperature of 45° C.-55° C. to obtain efinaconazole as para-toluenesulphonic acid salt.

The X-ray diffractogram of efinaconazole para-toluenesulphonic acid salt is shown in FIG. 1.

Efinaconazole para-toluenesulphonic acid salt is then dissolved in 2.0-4.0 volumes of a mixture of water and polar protic solvents, preferably water/ethanol, preferably 2.5-3.5 volumes, which is then filtered to remove insolubles. A 30% sodium hydroxide solution is then dropped therein until a pH from 10 to 12, preferably from 10.5 to 11.5, is reached.

When the required pH is value is reached, 1.0-6.0 volumes of water, preferably 3.0-4.0 volumes, are added.

The resulting solid is dried under vacuum at the temperature of 45° C.-55° C. to obtain pure efinaconazole with a melting point of 86-87° C.

Figure 2:
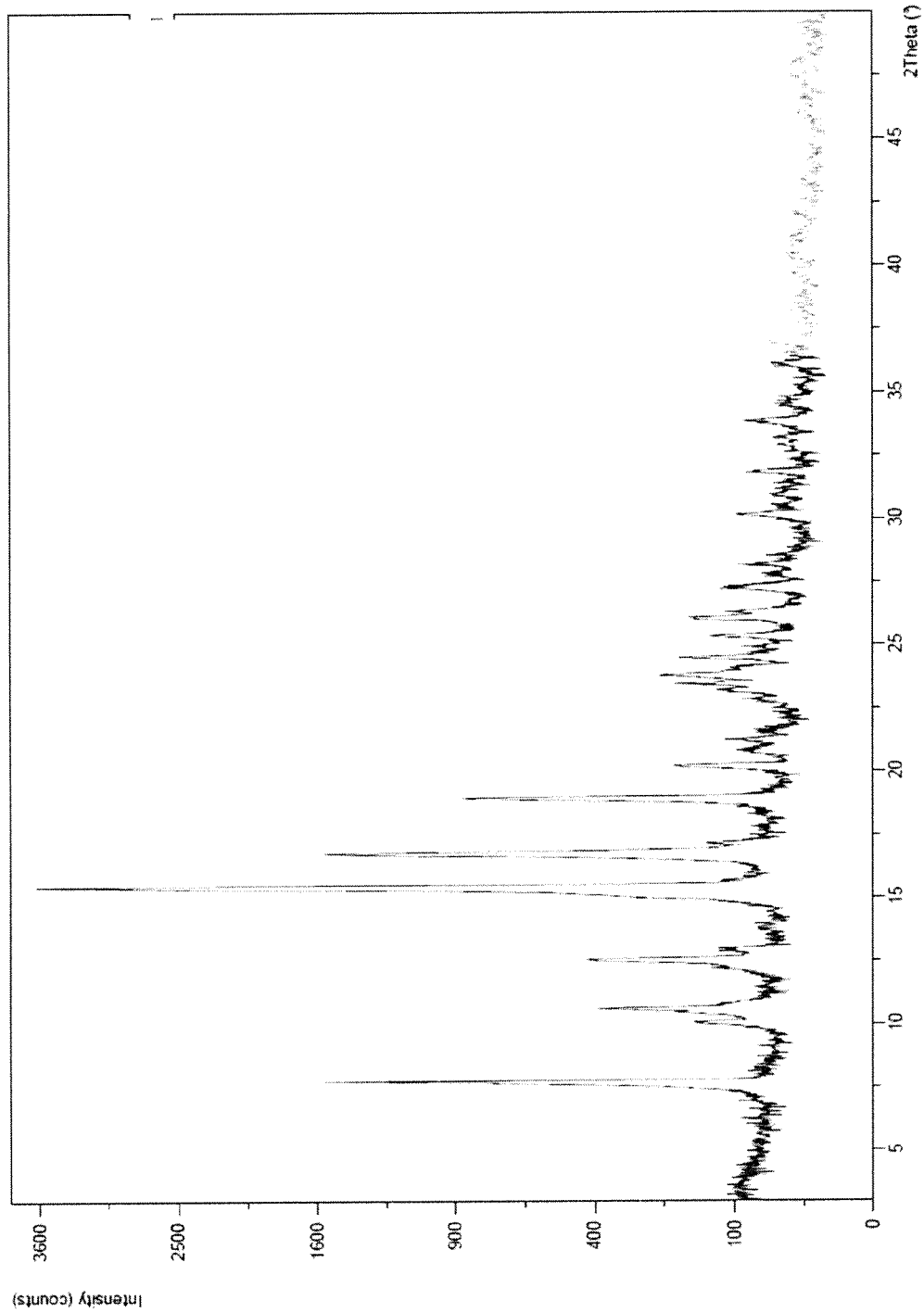

The X-ray diffractogram is shown in FIG. 2.

The cycle comprising salification, neutralization and isolation of the end product can be repeated as described above if necessary.

Alternatively, efinaconazole can be obtained by crystallisation of efinaconazole base from hydrocarbons, preferably heptane.

Optionally, crude efinaconazole is dissolved in 1.0-3.0 volumes of heptane, preferably 1.5-2.5 volumes. After cooling the suspension to 0-5° C. the resulting crystal is filtered, and washed with cold heptane. The solid obtained after drying has a melting point of 86-87° C.

Figure 3:
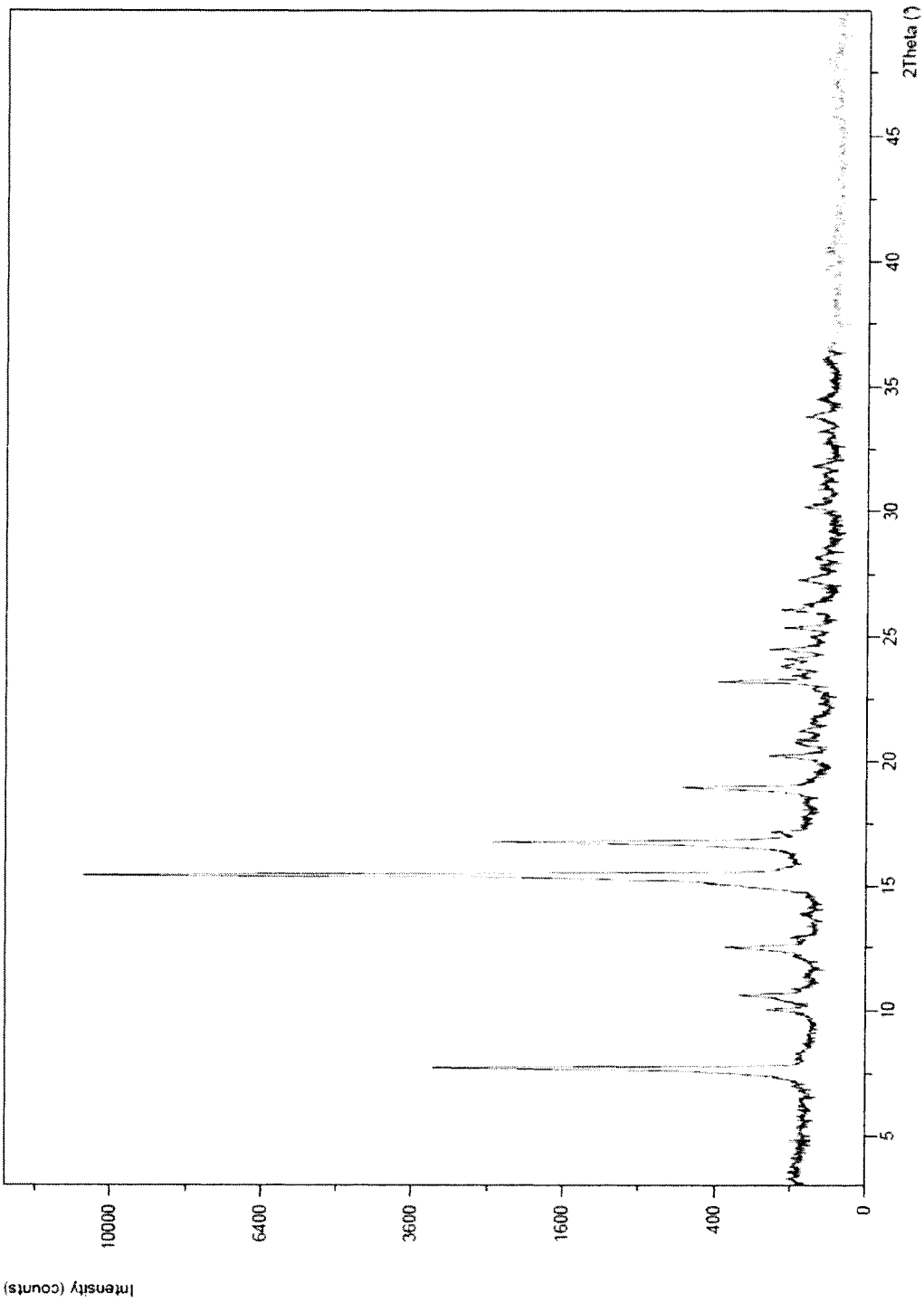

The X-ray diffractogram of the crystal obtained from heptane is shown in FIG. 3.

The X-ray diffractograms of both crystals obtained from heptane and from a water/ethanol mixture are identical.

The efinaconazole obtained from both crystallisations described presents sufficient purity for an active pharmaceutical ingredient.

The invention is illustrated in detail in the following examples.

Example 1: Synthesis of Efinaconazole in the Presence of Methylenepiperidine Hydrochloride and N,N-Diisopropylethylamine Methylenepiperidine hydrochloride (119.27 g, 0.8926 moles) is added to a solution of 1-[[(2R,3S)-2-(2,4-difluorophenyl)-3-methyloxiranyl]methyl]-1H-1,2,4-triazole (172.5 g, 0.6866 moles) in acetonitrile (690 ml).

Diisopropylethylamine (124.2 g, 0.961 moles) is added to the resulting solution.

The resulting solution is then cooled to 0-5° C. and anhydrous magnesium chloride (a total of 130.74 g, 1.373 moles) is added in about 4 portions, monitoring the exothermy.

The reaction mixture is then heated to 70-75° C. and maintained at that temperature for 16 h.

The reaction is then monitored by UPLC. After completion of the reaction, the mixture is concentrated to a small volume and taken up with ethyl acetate. Ethyl acetate (720 ml) is then added to the resulting residue, and water (720 ml) is slowly dropped therein, monitoring the exothermy.

After phase separation the organic phase is filtered and concentrated, taking up with ethanol up to about 2 volumes relative to the expected product. Water (335 ml) is dropped into the resulting ethanol solution at room temperature. After the start of precipitation of the product the suspension is cooled to 0-5° C. and filtered, washing the panel with a 45:55 mixture of water/ethanol (409 ml).

The resulting solid is then dried under vacuum at the temperature of 50° C.

The yield obtained from the starting intermediate epoxytriazole (II) is about 84%.

Example 2: Synthesis of Efinaconazole in the Presence of Methylenepiperidine Hydrochloride and Isopropylmagnesium Chloride 2.0M isopropylmagnesium chloride in tetrahydrofuran (12.3 g, 25.2 mmol) is added in about 1 h to a suspension of methylenepiperidine hydrochloride (3.45 g, 25.9 mmols) in anhydrous tetrahydrofuran (20 ml), cooled to 0-5° C.

1-[[(2R,3S)-2-(2,4-Difluorophenyl)-3-methyloxiranyl]methyl]-1H-1,2,4-triazole (5.00 g, 19.9 mmols) is added in portions to the resulting suspension.

The reaction mixture is then heated to reflux, and said temperature is maintained until the reaction is complete (monitored by UPLC).

After completion of the reaction, the mixture is concentrated to residue and taken up with ethyl acetate.

Ethyl acetate (20 ml) is then added to the residue, and water (20 ml) is slowly dropped therein, monitoring the exothermy.

After phase separation the organic phase is filtered and concentrated, taking up with ethanol up to about 2 volumes relative to the expected product. Water (10 ml) is dropped into the resulting ethanol solution at room temperature. After the start of precipitation of the product the suspension is cooled to 0-5° C. and filtered, washing the panel with a 45:55 mixture of water/ethanol (12 ml).

The resulting solid is then dried under vacuum at the temperature of 50° C.

The yield obtained from the starting intermediate epoxytriazole (II) is about 83%.

Example 3: Synthesis of Efinaconazole from Methylenepiperidine Free Base Neutralised with Diisopropylamine A suspension of methylenepiperidine hydrochloride (119.27 g, 0.8926 moles), acetonitrile (690 ml) and diisopropylethylamine (124.2 g, 0.961 moles) is prepared.

The suspension previously prepared is then added to a solution of 1-[[(2R,3S)-2-(2,4-difluorophenyl)-3-methyloxiranyl]methyl]-1H-1,2,4-triazole (172.5 g, 0.6866 moles) in acetonitrile (200 ml).

The resulting solution is then cooled to 0-5° C. and anhydrous magnesium chloride (a total of 130.74 g, 1.373 moles) is added in about 4 portions, monitoring the exothermy.

The reaction mixture is then heated to 70-75° C. and maintained at that temperature for 16 h.

The reaction is then monitored by UPLC. After completion of the reaction, the mixture is concentrated to a small volume and taken up with ethyl acetate.

Ethyl acetate (720 ml) is then added to the resulting residue, and water (720 ml) is slowly dropped therein, monitoring the exothermy.

After phase separation the organic phase is filtered and concentrated, taking up with ethanol up to about 2 volumes relative to the titrated expected product. Water (335 ml) is dropped into the resulting ethanol solution at room temperature. After the start of precipitation of the product the suspension is cooled to 0-5° C. and filtered, washing the panel with a 45:55 mixture of water/ethanol (409 ml).

The resulting solid is then dried under vacuum at the temperature of 50° C.

The yield obtained from the starting intermediate epoxytriazole (II) is about 83%.

Example 4: Synthesis of Efinaconazole from Methylenepiperidine Free Base Neutralised with Isopropylmagnesium Chloride 2.0M isopropylmagnesium chloride in tetrahydrofuran (12.3 g, 25.2 mmol) is added in about 1 h to a suspension of methylenepiperidine hydrochloride (3.45 g, 25.9 mmols) in anhydrous tetrahydrofuran (20 ml), pre-cooled to 0-5° C. The resulting suspension is then added slowly to a suspension of intermediate 1-[[(2R,3S)-2-(2,4-difluorophenyl)-3-methyloxiranyl]methyl]-1H-1,2,4-triazole (5.00 g, 19.9 mmols) in acetonitrile (10 ml).

The reaction mixture is then heated to reflux, and said temperature is maintained until the reaction is complete (monitored by UPLC).

After completion of the reaction, the mixture is concentrated to residue and taken up with ethyl acetate.

Ethyl acetate (20 ml) is then added to the residue, and water (20 ml) is slowly dropped therein, monitoring the exothermy.

After phase separation the organic phase is filtered and concentrated, taking up with ethanol up to about 2 volumes relative to the expected product. Water (10 ml) is dropped into the resulting ethanol solution at room temperature. After the start of precipitation of the product the suspension is cooled to 0-5° C. and filtered, washing the panel with a 45:55 mixture of water/ethanol (12 ml).

The resulting solid is then dried under vacuum at the temperature of 50° C.

The yield obtained from the starting intermediate epoxytriazole (II) is about 82%.

Example 5: Synthesis of Para-Toluenesulphonic Acid Efinaconazole Salt

Crude efinaconazole (354.0 g) is dissolved in ethanol (1580 ml).

The resulting solution is then heated to 50° C., and para-toluenesulphonic acid monohydrate (193.4 g, 1.0 eq) is added at that temperature. The suspension is then heated to reflux temperature and gradually cooled to 0-5° C. The suspension is then filtered, washing with cold ethanol (354 ml).

The resulting product is then dried under vacuum at the temperature of 50° C.

The yield is about 85%.

Example 6: Synthesis of Pure Efinaconazole from Para-Toluenesulphonic Acid Efinaconazole Salt Para-toluenesulphonic acid efinaconazole salt (454.0 g, 0.873 mol) is dissolved in a mixture of ethanol (870 ml) and water (500 ml).

The resulting solution is then filtered to remove insolubles, and 30% sodium hydroxide is added slowly to the resulting clear solution until a pH of about 11 is reached. Water (1660 ml) is then added to the resulting solution, and the suspension obtained is cooled to 0-5° C.

The solid is then filtered and washed with water (1500 ml).

The resulting product is then dried under vacuum at the temperature of 50° C.

The yield is about 98%.

UPLC-MS [M+H]$^+$=349

1H-NMR (in CDCl3) (chemical shifts expressed in ppm relative to the TMS signal): 0.94 (3H, dd); 2.22 (4H, m); 2.35 (2H, m); 2.68-2.73 (2H, m); 2.90-2.95 (1H, q, J=7); 4.64 (2H, s); 4.79-4.92 (2H, q, J=14); 5.40 (1H, s); 6.70-6.80 (2H, m); 7.48-7.54 (1H, m); 7.77 (1H, s); 8.01 (1H, s).

The invention claimed is:

1. A process for the synthesis of efinaconazole which comprises reacting 1-[[(2R,3S)-2-(2,4-difluorophenyl)-3-methyloxyranyl]methyl]-1H-1,2,4-triazole with 4-methylenepiperidine hydrochloride, in an organic aprotic solvent in the presence of neutralising agents and metal species promoting the reaction under anhydrous conditions, wherein said neutralizing agent is isopropylmagnesium chloride.

2. The process according to claim 1 wherein the organic aprotic solvent is acetonitrile or tetrahydrofuran or 2-methyltetrahydrofuran.

3. The process according to claim 1 wherein the agent promoting the opening of the epoxide ring are selected from alkylmagnesium halides and anhydrous magnesium chloride.

4. A process for the synthesis of efinaconazole which comprises reacting 1-[[(2R,3S)-2-(2,4-difluorophenyl)-3-methyloxyranyl]methyl]-1H-1,2,4-triazole with 4-methylenepiperidine, in an organic aprotic solvent in the presence of neutralising agents and metal species promoting the reaction under anhydrous conditions, wherein the neutralising agents are selected from organic amines and proton acceptors.

5. The process according to claim 4 wherein the neutralising agent is N,N-diisopropylethylamine and isopropylmagnesium bromide.

* * * * *